United States Patent [19]

Sato et al.

[11] Patent Number: 5,283,377
[45] Date of Patent: Feb. 1, 1994

[54] METHOD FOR PRODUCING OCTADIENOLS

[75] Inventors: Keiichi Sato, Tokyo; Iwao Nakajima, Yokohama; Yoko Misu, Tokyo, all of Japan

[73] Assignee: Mitsubishi Kasei Corporation, Tokyo, Japan

[21] Appl. No.: 955,054

[22] Filed: Oct. 1, 1992

[30] Foreign Application Priority Data

Oct. 2, 1991 [JP] Japan .................................. 3-255341

[51] Int. Cl.$^5$ ............................................. C07C 29/04
[52] U.S. Cl. ..................................... 568/896; 568/895
[58] Field of Search .......................... 568/895, 898, 896

[56] References Cited

U.S. PATENT DOCUMENTS 3,992,456 11/1976 Atkins et al. .
4,990,698 2/1991 Wada et al. .

FOREIGN PATENT DOCUMENTS 0025740 3/1981 European Pat. Off. ............ 568/898
0141712 11/1979 Japan ................................. 568/898
2074156 10/1981 United Kingdom ............... 568/898
2093025 8/1992 United Kingdom ............... 568/898

Primary Examiner—Werren B. Lone

Attorney, Agent, or Firm—Oblon, Spivak, McClelland, Maier & Neustadt

[57] ABSTRACT

A method for producing octadienols, which comprises reacting 1,3-butadiene with water in the presence of a palladium compound, a phosphine compound and carbon dioxide, wherein a compound of the formula (I):

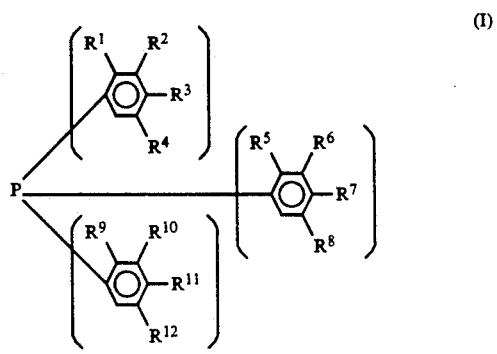

wherein each of $R^1$, $R^5$ and $R^9$ which may be the same or different, is a hydrocarbon group, and each of $R^2$, $R^3$, $R^4$, $R^6$, $R^7$, $R^8$, $R^{10}$, $R^{11}$ and $R^{12}$ which may be the same or different, is hydrogen or a substituent, provided that at least one of them is an electron donative substituent, is used as the phosphine compound.

18 Claims, No Drawings

METHOD FOR PRODUCING OCTADIENOLS

The present invention relates to an improved method for producing octadienols which are a hydrate of dimers of 1,3-butadiene, which comprises reacting 1,3-butadiene with water in the presence of a palladium compound, a phosphine compound and carbon dioxide.

Among octadienols, octa-2,7-dien-1-ol is a compound of particular importance from the viewpoint of chemical industry, as an intermediate for the production of n-octanol and its esters.

A method for producing octadienols as a hydrate of dimmers by reacting 1,3-butadiene with water in the presence of a palladium compound, a phosphine compound and carbon dioxide, is disclosed, for example, in Chemical Communications, 330 (1971) and Japanese Examined Patent Publication No. 10565/1975. In such a case, triphenyl phosphine is known to be advantageous as the phosphine compound to be used as a ligand for the palladium catalyst. However, the yield of octadienols and the selectivity for desired octa-2,7-dien-1-ol have not been adequate. Further, it is known that if triphenyl phosphine is used in excess by about 6 mol times relative to palladium, the yield of octadienols tends to be low (the above-mentioned Chemical communications), and there has been a problem that operational conditions are restricted.

Further, in a case wherein the reaction for producing octadienols by this method is conducted in a liquid phase system, butadiene and water are simultaneously contacted to the above catalyst component, and an operation of separating octadienols from the catalyst by such a means as distillation is conducted continuously or in a batch system. And at least a catalyst solution containing the palladium compound and the phosphine is recycled to the reaction system.

The present applicants have previously proposed a method for recycling a catalyst in a form free from high boiling point by-products which are likely to impair the reaction, which comprises precipitating a palladium complex from at least a part of the reaction solution with the above catalyst component and supplying such a complex again to the reaction system, for the production of alkadienols (Japanese Unexamined Patent Publication No. 174736/1991).

In the complex catalyst reaction, the metal component used in the catalyst plays an important role. At the same time, the ligand used will give an important influence over the activity and selectivity for the catalyst reaction. The present inventors have conducted extensive studies with an aim to provide an industrially advantageous method for producing octadienols, whereby the desired 2,7-octadiene-1-ol can be obtained in good yield and high selectivity by using a phosphine ligand most suitable for the dimarization hydration reaction to react 1,3-butadiene with water in the presence of a palladium compound, a phosphine compound and carbon dioxide. In the catalyst reaction solution, extensive substances such as palladium and a phosphine are contained, and if these catalyst components are not used effectively, the economical loss will be substantial. Therefore, it is important to take out only the catalyst components in a stable form by an economical means without impairing the catalytic activity and to recycle it for the reaction in order to industrially advantageously conduct the production of octadienols.

Further in the method disclosed in the above-mentioned Japanese Unexamined Patent Publication No. 174736/1991, the palladium complex to be precipitated and recycled may have a problem in the stability in air depending upon the type of the phosphine as one of the catalyst components, and if it is possible to handle such a palladium complex in a form more readily be handled, the method will be more advantageous as an industrial process.

The present invention provides a method for producing octadienols, which comprises reacting 1,3-butadiene with water in the presence of a palladium compound, a phosphine compound and carbon dioxide, wherein a compound of the formula (I):

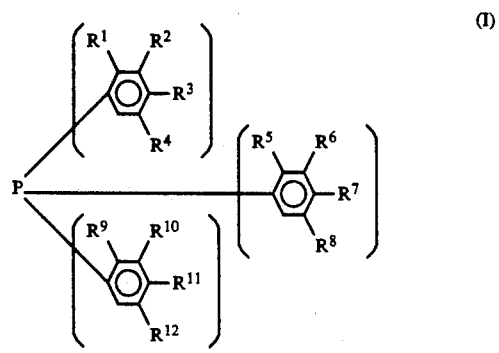

(I)

wherein each of $R^1$, $R^5$ and $R^9$ which may be the same or different, is a hydrocarbon group, and each of $R^2$, $R^3$, $R^4$, $R^6$, $R^7$, $R^8$, $R^{10}$, $R^{11}$ and $R^{12}$ which may be the same or different, is hydrogen or a substituent, provided that at least one of them is an electron donative substituent, is used as the phosphine compound.

Further, the present invention provides a novel bis(-phosphine) palladium complex which comprises palladium and a phosphine of the above formula (I).

Namely, the present inventors have surprisingly found that octadienols can be obtained in good yield, 2,7-octadiene-1-ol can be obtained highly selectively and a wide range of operational conditions can be selected, when a phosphine compound having the above mentioned specific structure is present as the phosphine ligand in the reaction for producing octadienols from 1,3-butadiene and water in the presence of a palladium compound, a phosphine compound and carbon dioxide. Further, it has been found that when a catalyst containing a novel bis(phosphine) palladium complex which is stable in air and easy to handle and has a high level of heat stability, is precipitated from at least a part of the reaction solution obtained by the reaction, and the catalyst is supplied again to the above reaction system, only the catalyst component can be recycled without loosing the effectiveness as the catalyst. The present invention has been accomplished on the basis of these discoveries.

Now, the present invention will be described in detail with reference to the preferred embodiments.

Usually readily available as the butadiene material to be reacted with water by the method of the present invention to produce octadienols, is purified 1,3-butadiene or so-called BBP i.e. a $C_4$ fraction mixture from the decomposition product of naphtha. When BBP is used as the starting material mainly from the economical consideration, it is advisable to preliminarily separate and remove acetylenes and allenes contained in the starting material BBP. There is no particular restriction as to the method for reducing acetylenes and allenes, and various known methods may suitably be used. After the removal or reduction of acetylenes and allenes, the total concentration of acetylenes and allenes in the 1,3-butadiene starting material to be subjected to the dimarization hydration reaction to produce octadienols, should be as low as possible, and it is usually preferably at a level of not higher than 1.0% by weight relative to 1,3-butadiene.

Water as the other starting material may suitably be water having a sufficient purity not to adversely affect the dimarization hydration reaction. There is no particular restriction as to the amount of water to be used. However, the amount is usually selected within a range of from 0.5 to 10 mols, preferably from 1 to 5 mols, per mol of 1,3-butadiene.

The form and the atomic valency of the palladium compound to be used as the main catalyst in the present invention, are not necessarily restrictive. In addition to the novel bis(phosphine) palladium complex wherein the phosphine has a structure of the formula (I), there may, for example, be employed a 0-valence palladium complex such as palladium tetrakis(triphenylphosphine), dipalladium tris(dibenzylideneacetone) or palladium (1,5-cyclooctadiene) (maleic anhydride), an organic salt of palladium such as palladium nitrate, an organic salt of palladium such as palladium acetate and a palladium chelate compound such as palladium bis(acetylacetone) as well as a bivalent palladium complex such as palladium bis(tri-n-butylphosphine) acetate.

The amount of such a palladium compound to be used, varies within a wide range. However, the amount is usually selected within a range of from 0.00001 to 1 g atom, preferably from 0.0001 to 0.1 g atom as palladium per mol of 1,3-butadiene.

The phosphine compound to be used in the method of the present invention, is a compound of the above formula (I).

In the above formula (I), each of $R^1$, $R^5$ and $R^9$ which may be the same or different, is a hydrocarbon group, usually preferably a lower alkyl group having from 1 to 4 carbon atoms, particularly preferably a methyl group.

At least one of $R^2$, $R^3$, $R^4$, $R^6$, $R^7$, $R^8$, $R^{10}$, $R^{11}$ and $R^{12}$, is an electron donative substituent with a Hammett $\sigma$ value being negative, and each of them which may be the same or different, is hydrogen or a substituent, preferably an electron donative substituent.

The electron donative substituent may usually be an alkyl group, an alkylamino group, an amino group, an alkoxy group or a hydroxyl group, and such a group may have an electron attracting substituent such as a halogen atom, a cyano group, a carbonyl group or a sulfonate group attached thereto, so long as it is electron donative as a whole. Among them, an alkyl group and an alkoxy group are preferred, and the alkyl group or the alkoxy group preferably has from 1 to 20 carbon atoms.

Specific examples of the phosphine compound include tris(2,4-dimethylphenyl)phosphine, tris(2,3-dimethylphenyl)phosphine, tris(2,5-dimethylphenyl)phosphine, tris(2,4,5-trimethylphenyl)phosphine, tris(2,3,4-trimethylphenyl)phosphine, tris(2,3,4,5-tetramethylphenyl)phosphine, tris(2-methyl-4-ctylphenyl)phosphine, tris(2-methyl-4-(2-sodium sulfonate)ethylphenyl)phosphine, tris(2-methyl-4-(2-lithium sulfonate)ethylphenyl)phosphine, bis(2,4-dimethylphenyl)(2-methylphenyl)phosphine, (2,4-dimethylphenyl)bis(2-methylphenyl)phosphine, bis(2,4-dimethylphenyl)(2-ethylphenyl)phosphine, tris(2-methyl-4-methoxyphenyl)phosphine, tris(2-methyl-4-ethoxyphenyl)phosphine, tris(2-methyl-4-octoxyphenyl)phosphine, tris(2-methyl-4-(2-ethoxy)ethoxyphenyl)phosphine, tris(2-methyl-4-(2-sodium sulfonate)ethoxyphenyl)phosphine, tris(2-methyl-4-(2-lithium sulfonate)ethoxyphenyl)phosphine, bis(2-methyl-4-methoxyphenyl)(2-methylphenyl)phosphine, (2-methyl-4-methoxyphenyl)bis(2-methylphenyl)phosphine, tris(2-methyl-4-dimethylaminophenyl)phosphine, tris(2-methyl-4-decoxyphenyl)phosphine, tris(2-methyl-4-(1-methylheptoxy)phenyl)phosphine and tris(2-methyl-4-(t-butyl)phenyl)phosphine. However, the phosphine compound is not restricted to such specific examples.

The amount of the phosphine compound is usually selected within a wide range of from 0.1 to 100 mols, preferably from 3 to 50 mols, more preferably from 4 to 20 mols, per g atom of palladium. Thus, a wide range of operational conditions can be selected.

Carbon dioxide to be used in the method of the present invention may be of any type so long as it is present in the form of carbon dioxide in the reaction system. For example, it may be molecular carbon dioxide, carbonic acid, a carbonate, a bicarbonate or an adduct of carbon dioxide or carbonic acid with amine. The upper limit of the amount of carbon dioxide is determined from the economical viewpoint, and an excessive use does not impair the reaction. Carbon dioxide is used usually in an amount of at least 1 mol, preferably at least 10 mol, per g atom of palladium.

To conduct the method of the present invention, it is preferred to employ a solvent in order to smoothly carry out the reaction. Useful solvents include, for example, ethers such as diethyl ether, dioxane, tetrahydrofuran, ethylene glycol dimethyl ether and tetraethylene glycol dimethyl ether, ketones such as acetone, methyl ethyl ketone, diethyl ketone, methyl isopropyl ketone and ethyl n-butyl ketone, nitriles such as acetonitrile, propionenitrile and benzonitrile, aromatic hydrocarbons such as benzene, toluene, xylene and ethylbenzene, alkanes such as pentane, hexane and heptane, alkenes such as hexene and octene, sulfoxides such as dimethylsulfoxide, nitro compounds such as nitrobenzene and nitromethane, pyridine derivatives such as pyridine and α-picoline, and amides such as acetamide, propionamide, N,N-dimethyformamide, N,N-dimethylacetamide and N,N-diethylacetamide. As other solvents, alcohols such as methanol, ethanol, n-propanol, isopropanol, n-butanol, isobtanol, t-butanol and n-octanol, and carboxylic acids such as formic acid, acetic acid, propionic acid and butylic acid, may be mentioned. Among them, when lower alcohols are used, formation of by-products such as alkoxy octadienes will be accompanied, and when lower carboxylic acids are used, formation of by-products such as acyloxyoctadienes will be accompanied, whereby a due care will be required, since the reaction system will otherwise be complicated.

The amount of the solvent is not necessarily limited. However, it is usually optionally selected within a range of from 0.1 to 50 parts by weight, preferably from 1 to 10 parts by weight, per part by weight of 1,3-butadiene.

The reaction temperature for the reaction of 1,3-butadiene with water according to the present invention, can be selected within a wide range of from room temperature to 180° C. However, it is common to select the temperature within a range of from 50° to 130° C. However, within a high temperature range of at least 90° C., undesirable by-products tend to form in a substantial amount, and it is preferred to select a lower temperature range to obtain octadienols in good yield. In such a case, the reaction rate is likely to be problematic. However, in the method of the present invention, a phosphine compound having the specific structure is used, whereby it is possible to prepare octadienols in good yield at a sufficiently high rate even within such a lower temperature range. The reaction pressure is selected within a range of from normal pressure to 200 kg/cm$^2$. In such a case, in addition to carbon dioxide, a gas inert to the reaction such as nitrogen, herium or argon may be present.

In the present invention, 1,3-butadiene and water are reacted under the above described reaction conditions using the above described materials for reaction, to form octadienols. The reaction solution obtained by this reaction contains the catalyst, 2,7-octadien-1-ol as the main product and by-products such as 1,7-octadien-3-ol, octatrienes, dioctadienyl ethers, organic carboxylic acids and esters as well as the solvent and unreacted 1,3-butadiene and water. The amounts of the by-products depend on the reaction conditions, and they are usually within a few mol %, respectively, based on 1,3-butadiene.

The method of the present invention may contain an additional step of precipitating a catalyst component containing a complex composed of palladium and the phosphine, from the reaction solution obtained by the above reaction and then supplying the catalyst component again to the reaction system. For this purpose, a novel bis(phosphine) palladium complex composed of palladium and the phosphine of the above formula (I) has high thermal stability and is easy to handle, and it can advantageously be recycled without any substantial deterioration of the catalytic activity by recycling. To form such a complex, it is preferred to treat the reaction solution so that the phosphine in the reaction solution is at least two mols, preferably at least three mols per g atom of palladium, in a free state to be capable of being coordinated to palladium. Specifically, the reaction solution or a part of the reaction solution containing the catalyst component, is contacted with a basic substance or with a reducing agent such as hydrogen to conduct an operation to make the phosphine a free state to be capable of being coordinated. It is of course effective to additionally supply a phosphine to the reaction solution. As the basic substance to be used for contacting it with the reaction solution or with a part of the reaction solution containing the catalyst component, a hydroxide of an alkali metal, an alkaline earth metal or an ammonium ion, an oxide, an alkoxide, a carboxylic acid salt, a carbonate or a bicarbonate, may be used. Specifically, lithium hydroxide, sodium hydroxide, potassium hydroxide, magnesium oxide, calcium oxide, barium oxide, sodium ethoxide, sodium acetate, sodium carbonate, calcium carbonate or sodium bicarbonate, may be mentioned.

The basic substance is usually in the form of a solution dissolved in a solvent such as water, but it may be used in a solid form. There is no particular restriction as to the concentration of the basic substance when it is used in the form of a solution, but it is usually advantageous to use a solution of from 0.05 to 5 mols/l. The amount of the basic substance is not necessarily restrictive, but it is preferably at least equimolar to the phosphine.

The temperature for the contact treatment of the reaction solution with the basic substance or with the reducing agent such as hydrogen, is preferably from 0° to 150° C., more preferably from 20° to 100° C. In order to precipitate the catalyst more efficiently, it is advisable to cool the solution after the contact treatment.

The catalyst precipitated from the reaction solution or from the part of the reaction solution containing the catalyst component, can be readily separated and recovered by a conventional technique such as filtration or decantation. A part or whole of the recovered catalyst may be supplied again to the reaction for producing octadienols by reacting 1,3-butadiene with water, as the case requires.

The novel (phosphine)palladium complex wherein the phosphine is represented by the above formula (I), can be prepared also by the same method as the one for a known palladium 0 valent phosphine complex such as palladium tetrakis(triphenylphosphine) or palladium tris(triphenylphosphine). Namely, it can be obtained by reducing a palladium bivalent complex such as palladium chloride with a reducing agent such as hydrazine hydrate in the presence of a predetermined phosphine ligand, as disclosed in D. R. Coulson, Inorg. Synth., 13, 121(1972).

The method of the present invention can be carried out in a well known manner such as a continuous system, a semicontinuous system or a batch system. The octadienols as the main product can be recovered by various means such as distillation, from the reaction solution or from a filtrate having the catalyst removed by the above-mentioned operation. A part or whole of the catalyst and the remaining reaction mixture, may be recycled to the reaction system, by themselves or after separating the catalyst by the above mentioned operation.

Now, the present invention will be described in further detail with reference to Examples. However, it should be understood that the present invention is by no means restricted to such specific Examples.

EXAMPLE 1

Into a stainless steel autoclave having an internal capacity of 300 ml, 0.36 mmol of palladium acetate, 1.44 mmol of tris(2,4-dimethylphenyl)phosphine, 61 g of acetone and 6.5 g of water were charged under a nitrogen gas atmosphere, and 11 g of 1,3-butadiene and 11 g of carbon dioxide were further introduced. The reaction mixture was heated until the internal temperature became 80° C. over a period of 20 minutes, while stirring the mixture at a speed of 800 rpm. The reaction was continued at 80° C. for further two hours. Then, the reaction product was analyzed by gas chromatography. The results are shown in Table 1.

EXAMPLES 2 TO 5 AND COMPARATIVE EXAMPLES 1 AND 2

The operation was conducted in the same manner as in Example 1 except that the phosphine compound as identified in Table 1 was used instead of tris(2,4-dimethylphenyl)phosphine. The results are shown in Table 1.

TABLE 1

| Example No. | Phosphine Compound | ΣHOD*1 (%) | 1-HOD*2 / ΣHOD (%) | NOT*3 (%) | DODE*4 (%) | ΣHOD*5 Selectivity (%) |
| --- | --- | --- | --- | --- | --- | --- |
| Example 1 | Tris(2,4-dimethylphenyl)phosphine | 84.9 | 95 | 1.5 | 0.7 | 92.7 |
| Example 2 | Tris(2,5-dimethylphenyl)phosphine | 82.4 | 95 | 1.7 | 1.5 | 91.7 |
| Example 3 | Tris(2-methyl-4-methoxyphenyl)phosphine | 79.0 | 95 | 1.3 | 0.4 | 93.9 |
| Example 4 | Tris(2,4,5-trimethylphenyl)phosphine | 84.1 | 93 | 2.1 | 2.4 | 92.7 |
| Example 5 | Tris(2-methyl-4-decoxyphenyl)phosphine | 77.1 | 95 | 2.0 | 1.3 | 93.8 |
| Comparative Example 1 | Triphenylphosphine | 47.6 | 84 | 2.1 | 1.8 | 86.9 |
| Comparative Example 2 | Tris(2-methylphenyl)phosphine | 76.6 | 95 | 1.5 | 1.0 | 90.1 |

*1 ΣHOD: Yield of the formed octadienols to the charged butadiene (%)
*2 1-HOD/ΣHOD: Proportion of octa-2,7-diene-1-ol (1-HOD) in the octadienols (%)
*3 NOT: Yiled of the formed octa-1,3,7-triene to the charged butadiene (%)
*4 DODE: Yield of the formed dioctadienyl ether to the charged butadiene (%)
*5 ΣHOD Selectivity: Selectivity of octadienols in all products from butadiene (%)

EXAMPLE 6

The operation was conducted under the same conditions as in Example I except that 0.5 mmol of palladium acetate, 2 mmol of tris(2,4-dimethylphenyl)phosphine, 50 g of acetone, 18 g of water, 27 g of 1,3-butadiene and 15 g of carbon dioxide were used, and the reaction was conducted for 4 hours. The results are shown in Table 2.

EXAMPLE 7

The operation was conducted in the same manner as in Example 4 except that the reaction temperature was changed to 90° C. The results are shown in Table 2.

EXAMPLE 8

The operation was conducted in the same manner as in Example 3 except that the amount of tris(2,4-dimethylphenyl)phosphine was changed to 8 mmol, and the reaction time was changed to 3 hours. The results are shown in Table 2.

acetate, 17.5 mmol of tris(2,4-dimethylphenyl)phosphine and 50 ml of methanol were charged under a nitrogen gas atmosphere, and 25 ml of 1,3-butadiene was further introduced. The reaction mixture was heated until the internal temperature became 80° C. over a period of 20 minutes, while stirring it at a speed of 800 rpm, and the reaction was continued at 80° C. for further 1.5 hours. After cooling the mixture to room temperature, a formed yellow palladium complex was separated by filtration and washed with 40 ml of methanol and further with 40 ml of n-hexane, and 2.82 g of the obtained crystals were dried under reduced pressure at room temperature.

| Results of the elemental analysis (calculated values) | Pd 13.3% (13.3) | C 72.82% (72.13) | H 7.03% (6.81) |
| --- | --- | --- | --- |

From the results of the elemental analysis, the obtained palladium complex was confirmed to be a bis(-

TABLE 2

| Example No. | Amount of the phosphine compound (mmol) | Reaction temp. (°C.) | Reaction time (hr) | ΣHOD*1 (%) | 1-HOD*2 / ΣHOD (%) | NOT*3 (%) | DODE*4 (%) |
| --- | --- | --- | --- | --- | --- | --- | --- |
| Example 6 | 2 | 80 | 4 | 79.4 | 96 | 2.0 | 2.6 |
| Example 7 | 2 | 90 | 4 | 79.7 | 93 | 3.1 | 5.8 |
| Example 8 | 8 | 80 | 3 | 81.8 | 95 | 3.0 | 3.6 |

*1 ΣHOD: Yield of the formed octadienols to the charged butadiene (%)
*2 1-HOD/ΣHOD: Proportion of octa-2,7-diene-1-ol(1-HOD) in the octadienols (%)
*3 NOT: Yield of the formed octa-1,3,7-triene to the charged butadiene (%)
*4 DODE: Yield of the formed dioctadienyl ether to the charged butadiene (%)

EXAMPLE 9

The operation was conducted in the same manner as in Example 1 except that tris(2,3,4,5-tetramethylphenyl)phosphine was used instead of tris(2,4-dimethylphenyl)phosphine, and the reaction was conducted for 4 hours. ΣHOD was 88.5%, 1-HOD/ΣHOD was 93%, NOT was 1.6%, and DODE was 2.9%

EXAMPLE 10

Preparation of bis(tris(2,4-dimethylphenyl)phosphine)palladium complex

Into a stainless steel induction stirring autoclave having an internal capacity of 300 ml, 5 mmol of palladium tris(2,4-dimethylphenyl)phosphine) palladium complex. The thermal stability and the stability in air were examined by DSC (Differential Scanning Calorimetry) and TG-DTA(Thermogravimetry Differential Thermal Analysis), respectively. The results were better than the known similar complex (bis(tris(2-methylphenyl)phosphine)palladium), as shown in Table 3.

COMPARATIVE EXAMPLE 3

Preparation of a bis(tris(2-methylphenyl)phosphine)palladium complex

The above identified complex was prepared in the same manner as in Example 10 except that tris(2- methylphenyl)phosphine was used instead of tris(2,4-dimethylphenyl)phosphine. The results of DSC and TG-DTA are shown in Table 3.

TABLE 3

| | DSC*1 | |
|---|---|---|
| | Endothermic temp. | Peak temp. |
| Example 10 | 230° C. | 238° C. |
| Comparative Example 3 | 202° C. | 212° C. |

| | TG-DTA*2 | | | |
|---|---|---|---|---|
| | Weight reduction | | | |
| | Initiation temp. | Temp. extrapolated | Weight loss | Exothermic peak temp. |
| Example 10 | 207° C. | 245° C. | 74% | 219° C. |
| Comparative Example 3 | 194° C. | 228° C. | 76% | 194° C. |

*1Conditions for measurement: Sample: 1 mg, Ag pressure resistant cell (sealed under $N_2$) 10° C./min, $N_2$: 50 ml/min
*2Conditions for measurement: Sample: 5 mg, Al pan 10° C./min, Air: 200 ml/min

EXAMPLE 12

0.75 mmol of palladium bis(tris(2,4-dimethylphenyl)phosphine), 1.5 mmol of tris(2,4-dimethylphenyl)phosphine, 55 g of acetone and 10 g of water were charged, and 20.7 g of 1,3-butadiene and 11 g of carbon dioxide were further added, and the mixture was reacted for 1.5 hours in the same manner as in Example 1. The reaction solution was distilled under reduced pressures at room temperature to distill off of the acetone solvent. Then, 1.5 mmol of tris(2,4-dimethylphenyl)phosphine was added, and 100 ml of a 1 mol/l sodium hydroxide aqueous solution was added thereto. The mixture was reacted at 60° C. for 1 hour and then cooled with ice. The aqueous phase was separated, and the organic phase containing a precipitated yellow complex was washed twice with 50 ml of water, and then the solid content was separated by filtration. Using the obtained solid content which contains palladium bis(tris(2,4-dimethylphenyl)phosphine), and 55 g of acetone, 10 g of water, 20.2 g of 1,3-butadiene and 11 g of carbon dioxide, the reaction was conducted for 1.5 hours in the same manner as the first time. The analytical results of the respective reaction products are shown in Table 4.

| | ΣHOD (%) | 1-HOD/ΣHOD (%) | NOT (%) | DODE (%) |
|---|---|---|---|---|
| 1st time | 80.3 | 94.4 | 3.5 | 1.3 |
| 2nd time | 84.7 | 95.9 | 3.1 | 2.2 |

EXAMPLE 13

0.377 mmol of palladium acetate, 1.5 mmol of tris(2-methyl-4-methoxyphenyl)phosphine, 55 g of acetone and 10 g of water were charged, and 20.2 g of 1,3-butadiene and 11 g of carbon dioxide were further added, and the mixture was reacted for 5 hours in the same manner as in Example 1. The reaction solution was distilled under reduced pressures at room temperature to distill off the acetone solvent. Then, 0.75 mmol of tris(2-methyl-4-methoxyphenyl)phosphine was added, and 100 ml of a 1 mol/l sodium hydroxide aqueous solution was added thereto. The mixture was reacted at 60° C. for 1 hour and then cooled with ice. The aqueous phase was separated, and the organic phase containing a precipitated yellow complex was washed twice with 50 ml of water, and then the solid content was separated by filtration. Using the obtained solid content which contains palladium bis(tris(2-methyl-4-methoxyphenyl)phosphine, and 55 g of acetone, 10 g of water, 20.1 g of 1,3-butadiene and 11 g of carbon dioxide, the reaction was conducted for 5 hours in the same manner as the first time. The analytical results of the respective reaction products are shown in Table 5.

| | ΣHOD | 1-HOD/ΣHOD (%) | NOT (%) | DODE (%) |
|---|---|---|---|---|
| 1st time | 70.9 | 95.3 | 1.6 | 1.2 |
| 2nd time | 68.0 | 95.0 | 1.6 | 1.5 |

According to the method of the present invention, it is possible to produce octadienols in good yield and 2,7-octadiene-1-ol highly selectively by reacting 1,3-butadiene with water in the presence of a palladium compound, a phosphine compound having the specific structure and carbon dioxide. Thus, the present invention provides an industrially advantageous method for producing octadienols. Further, the novel bis(phosphine)palladium complex of the present invention is excellent in the heat stability and easy to handle, and when precipitated from the reaction solution in the above method for preparing octadienols and supplied again to the reaction system, it undergoes no substantial deterioration of the catalytic activity and can advantageously be recycled.

We claim:
1. A method for producing octadienols, which comprises reacting 1,3-butadiene with water in the presence of a palladium compound, a phosphine compound and carbon dioxide, wherein a compound of the formula (I):

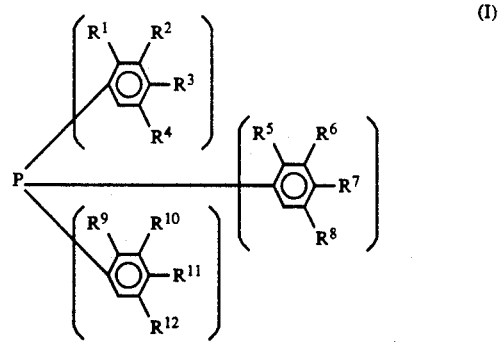

wherein each of $R^1$, $R^5$ and $R^9$ which may be the same or different, is a hydrocarbon group, and each of $R^2$, $R^3$, $R^4$, $R^6$ $R^7$, $R^8$, $R^{10}$, $R^{11}$ and $R^{12}$ which may be the same or different, is hydrogen or an electron donative substituent selected from the group consisting of an alkyl group, an alkylamino group, an amino group, an alkoxy group and a hydroxyl group, provided that at least one of them is an electron donative substituent, is used as the phosphine compound.

2. The method according to claim 1, wherein water is used in an amount of from 0.5 to 10 mols per mol of 1,3-butadiene.

3. The method according to claim 1, wherein the palladium compound is used in an amount of from 0.00001 to 1 g atom per mol of 1,3-butadiene.

4. The method according to claim 1, wherein each of $R^1$, $R^5$ and $R^9$ which may be the same or different, is a lower alkyl group having from 1 to 4 carbon atoms.

5. The method according to claim 1, wherein each of $R^1$, $R^5$ and $R^9$ is a methyl group.

6. The method according to claim 1, wherein the electron donative substituent is an alkyl group or an alkoxy group.

7. The method according to claim 1, wherein the phosphine compound is used in an amount of from 0.1 to 100 mols per g atom of palladium.

8. The method according to claim 1, wherein the reaction is conducted in a solvent.

9. The method according to claim 8, wherein the solvent is at least one member selected from the group consisting of ethers, ketones, nitriles, aromatic hydrocarbons, alkanes, alkenes, sulfoxides, nitro compounds, pyridine, pyridine derivatives, amides, alcohols and carboxylic acids.

10. The method according to claim 8, wherein the solvent is used in an amount of from 0.1 to 50 parts by weight per part by weight of 1,3-butadiene.

11. The method according to claim 1, wherein the reaction is conducted at a temperature of from room temperature to 180° C.

12. The method according to claim 1, wherein the reaction is conducted under a pressure of from atmospheric pressure to 200 kg/cm$^2$.

13. The method according to claim 1, wherein the reaction is conducted in a liquid phase.

14. The method according to claim 1, which contains an additional step of precipitating a catalyst component containing a complex composed of palladium and a phosphine from the reaction solution obtained by the reaction of claim 1 and supplying the catalyst component again to the reaction system.

15. The method according to claim 14, wherein the complex composed of palladium and a phosphine is a bis(phosphine) palladium complex comprising palladium and a phosphine of the above-mentioned formula (I).

16. The method according to claim 14, wherein each of $R^1$, $R^5$ and $R^9$ which may be the same or different, is a lower alkyl group having from 1 to 4 carbon atoms.

17. The method according to claim 16, wherein each of $R^1$, $R^5$ and $R^9$ is a methyl group.

18. The method according to claim 14, wherein the electron donative substituent is an alkyl group or an alkoxy group.

* * * * *